US012751707B2

(12) United States Patent
Coussa et al.

(10) Patent No.: US 12,751,707 B2
(45) Date of Patent: Oct. 6, 2026

(54) DEVICES FOR SCLERAL DEPRESSION

(71) Applicant: Alcon Inc., Fribourg (CH)

(72) Inventors: Razek G. Coussa, Oklahoma City, OK (US); Reto Grüebler, Greifensee (CH); Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 18/976,616

(22) Filed: Dec. 11, 2024

(65) Prior Publication Data

US 2025/0221698 A1 Jul. 10, 2025

Related U.S. Application Data

(60) Provisional application No. 63/618,434, filed on Jan. 8, 2024.

(51) Int. Cl.
*A61B 17/02* (2006.01)

(52) U.S. Cl.
CPC ...... *A61B 17/0231* (2013.01); *A61B 17/0293* (2013.01)

(58) Field of Classification Search
CPC ........................ A61B 17/0231; A61B 17/0293
See application file for complete search history.

(56) References Cited

U.S. PATENT DOCUMENTS 4,299,227 A 11/1981 Lincoff
4,453,546 A * 6/1984 Katz ...................... A61F 9/007 606/1
4,550,713 A * 11/1985 Hyman .................. A61B 46/00 128/849
5,009,660 A * 4/1991 Clapham ................ A61F 9/009 606/166
5,971,977 A * 10/1999 Korenfeld ............... A61F 9/008 606/4
6,068,643 A * 5/2000 Milverton .......... A61B 17/0231 606/107
6,083,155 A 7/2000 Trese
(Continued)

FOREIGN PATENT DOCUMENTS

CA 3007718 A1 * 12/2019 ............. A61F 9/007
KR 20170009451 A 1/2017
(Continued)

OTHER PUBLICATIONS

Cults. SEPI-Pizza Saver (The Pizza Saver), published Jul. 28, 2023. https://cults3d.com/en/3d-model/tool/sepi-pizza-saver-el-cosito-de-la-pizza?srsltid=AfmBOoqvMz7R65Y-iOyuSxWHuzVZ8tWzeS8AlUw5QOk1Woz0s9dTctwp (Year: 2023).*
(Continued)

*Primary Examiner* — Jacqueline T Johanas

(57) ABSTRACT

Described herein is a device for performing scleral depression. The device can include a ring and one or more arms protruding from the ring. The ring can define an opening over an eye and include a handle protruding away from the one or more arms. The opening can have a diameter that is at least 6 to 8 millimeters (mm) long. The one or more arms can be configured to be disposed over a globe of the eye for controllable depression of a sclera of the eye. Uniform pressure can be applied to the sclera by depression features at a distal end of each of the one or more arms.

20 Claims, 6 Drawing Sheets

(56) References Cited

U.S. PATENT DOCUMENTS

| | | | | |
|---|---|---|---|---|
| 6,436,113 | B1 * | 8/2002 | Burba | A61F 9/013 606/166 |
| 6,440,065 | B1 | 8/2002 | Hered | |
| 6,986,900 | B2 | 1/2006 | Yaacobi | |
| 7,419,493 | B2 | 9/2008 | Olsen | |
| 8,083,751 | B2 * | 12/2011 | Olsen | A61B 17/0231 606/107 |
| 8,235,893 | B2 | 8/2012 | Josephberg | |
| 9,504,459 | B1 * | 11/2016 | Nallakrishnan | A61B 17/0231 |
| 10,238,285 | B2 | 3/2019 | Farley et al. | |
| 10,251,634 | B2 | 4/2019 | Foxman | |
| 10,470,651 | B2 | 11/2019 | Vijfvinkel | |
| 10,898,371 | B2 | 1/2021 | Olson | |
| 11,129,604 | B2 * | 9/2021 | Kapusta | A61F 9/007 |
| 11,135,093 | B2 * | 10/2021 | Loerner | A61F 9/00825 |
| 11,166,708 | B2 | 11/2021 | Charles | |
| 11,266,395 | B2 | 3/2022 | Ganiban | |
| 11,419,695 | B2 | 8/2022 | Kehren-quitsdorf | |
| 11,826,033 | B2 | 11/2023 | Easley | |
| 12,059,372 | B2 * | 8/2024 | Chan | G16H 50/50 |
| 2003/0139808 | A1 | 7/2003 | Shahinpoor | |
| 2004/0204727 | A1 | 10/2004 | Olsen | |
| 2008/0081952 | A1 * | 4/2008 | Josephberg | A61B 17/0231 600/245 |
| 2008/0243139 | A1 | 10/2008 | Dusek | |
| 2009/0171364 | A1 * | 7/2009 | Olsen | A61B 17/0231 606/107 |
| 2010/0004499 | A1 | 1/2010 | Brigatti | |
| 2011/0021882 | A1 | 1/2011 | Selover | |
| 2013/0103145 | A1 * | 4/2013 | John | A61F 9/0017 351/219 |
| 2014/0378773 | A1 * | 12/2014 | Dykes | A61F 9/0017 600/208 |
| 2015/0359529 | A1 | 12/2015 | Ganiban | |
| 2016/0213180 | A1 * | 7/2016 | Javaruski | B65D 25/24 |
| 2020/0360104 | A1 | 11/2020 | Kehren-quitsdorf | |
| 2023/0040005 | A1 | 2/2023 | Charles | |
| 2023/0084104 | A1 | 3/2023 | Easley | |
| 2024/0350308 | A1 | 10/2024 | Calhoun | |
| 2025/0057694 | A1 * | 2/2025 | Ganiban | A61F 9/007 |
| 2025/0221698 | A1 * | 7/2025 | Coussa | A61B 17/0293 |

FOREIGN PATENT DOCUMENTS

| | | | | | |
|---|---|---|---|---|---|
| KR | 20200134911 | A | * | 12/2020 | A61F 9/00727 |
| RU | 2628651 | C1 | * | 8/2017 | |
| WO | 9302624 | A1 | | 2/1993 | |
| WO | 2004054487 | A2 | | 7/2004 | |
| WO | 2014071054 | A1 | | 5/2014 | |
| WO | 2015195748 | A2 | | 12/2015 | |

OTHER PUBLICATIONS

U.S. Appl. No. 62/042,549, Ganiban, et al., "Devices and Methods to Provide Hands Free Scleral Depression During Ophthalmic Procedures," filed Aug. 27, 2014, 43 pgs.

U.S. Appl. No. 62/114,848, Ganiban, et al., "Devices and Methods to Provide Hands Free Scleral Depression During Ophthalmic Procedures," filed Feb. 11, 2015, 43 pgs.

U.S. Appl. No. 62/013,326, Ganiban, et al., "Devices and Methods to Provide Hands Free Scleral Depression During Ophthalmic Procedures," filed Jun. 17, 2014, 33 pgs.

* cited by examiner

DEVICES FOR SCLERAL DEPRESSION

BACKGROUND

Scleral depression, also known as scleral indentation, is a technique used to better visualize the peripheral ocular fundus during certain ophthalmic procedures, including certain vitreoretinal surgical procedures. Generally, slight pressure is applied to the exterior of the sclera to bring the peripheral retina, ora serrata, and pars plana into a physician's field of view. To depress the sclera, a scleral depression instrument, or scleral depressor, is typically used. When the scleral depressor is inserted between the globe and the orbit, the space occupied by the instrument displaces the retina inward, creating an elevation therein and bringing the tissue into the physician's view. The elevation also allows for increased contrast within the indented region between the choroid, retinal pigmented epithelium, and retina.

During certain ophthalmic surgical procedures, such as bimanual vitreoretinal surgical procedures, a skilled assistant may be needed to perform scleral depression while the surgeon performs other operations of the procedure with both hands. Although the surgeon can use a chandelier-based lighting port and perform scleral depression with one hand while using a vitrector in the other hand, the lighting provided in such a manner may be ineffective and there may also be an increased risk of tortional rotation. Still further, current scleral depression instruments impede on the surgeon's intraoperative visualization and limit surgical microscope movement.

SUMMARY

The present disclosure generally relates to devices for performing scleral depression.

In certain embodiments, a device for scleral depression is provided. The device comprises: a ring defining an opening with a diameter that is at least 6 to 8 millimeters (mm) long; and one or more arms protruding from the ring in a first direction, wherein the one or more arms are configured to be disposed over a globe of an eye for controllable depression of a sclera of the eye.

In certain embodiments, another device for scleral depression is provided. The device comprises: a ring defining an opening with a diameter that is at least 6 to 8 millimeters (mm) long; one or more arms protruding from the ring, wherein each of the one or more arms comprise: a depression feature at a distal end of each of the one or more arms, wherein the depression features of each of the one or more arms are configured to apply pressure to a sclera of an eye to induce depression of the sclera, and wherein the one or more arms are configured to be disposed over a globe of the eye and to controllably induce the depression of the sclera for ophthalmic procedures.

In certain embodiments, another device for scleral depression is provided. The device comprises: a ring defining an opening with a diameter that is at least 6 to 8 millimeters (mm) long, wherein the ring comprises: a handle for rotating the device about a vertical axis of an eye; and one or more arms protruding from the ring, wherein the one or more arms are configured to be disposed over a globe of an eye for controllable depression of a sclera of the eye.

BRIEF DESCRIPTION OF THE DRAWINGS

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
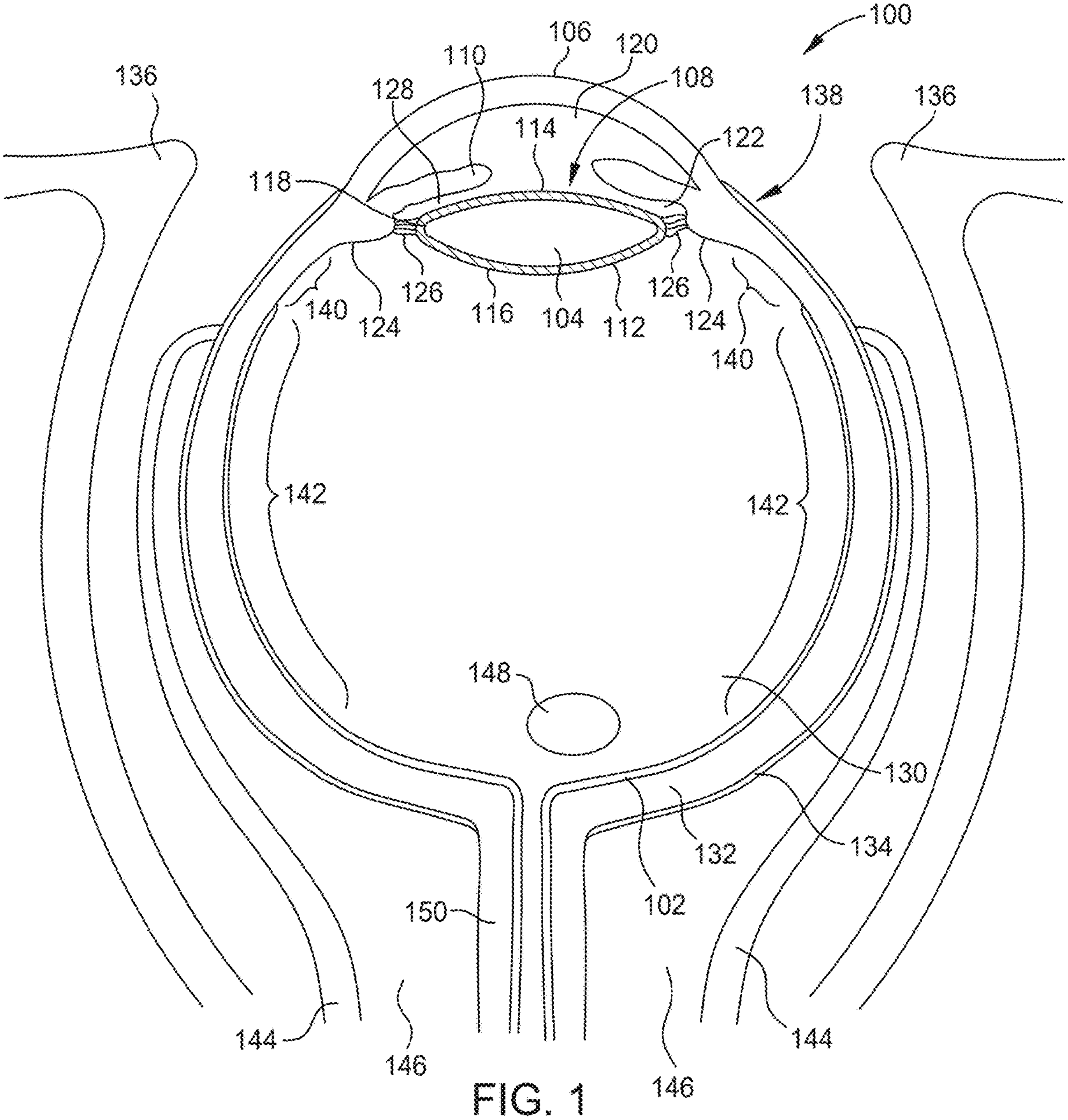
FIG. 1 illustrates a cross-sectional side view of an eye.

It will be readily understood that the components of the embodiments as generally described herein and illustrated in the appended Figures can be arranged and designed in a wide variety of different configurations. Thus, the following more detailed description of various embodiments, as represented in the Figures, is not intended to limit the scope of the present disclosure but is merely representative of various embodiments. While the various aspects of the embodiments are presented in the Figures, the Figures are not necessarily drawn to scale unless specifically indicated.

The present disclosure may be embodied in other specific forms without departing from its spirit or essential characteristics. The described embodiments are to be considered in all respects only as illustrative and not restrictive. The scope of the present disclosure is, therefore, indicated by the appended Claims rather than by this Detailed Description. All changes which come within the meaning and range of equivalency of the Claims are to be embraced within their scope.

Reference throughout this specification to features, advantages, or similar language does not imply that all of the features and advantages that may be realized with the present disclosure should be or are in any single embodiment of the disclosure. Rather, language referring to the features and advantages is understood to mean that a specific feature, advantage, or characteristic described in connection with an embodiment is included in at least one embodiment of the present disclosure. Thus, discussions of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize, in light of the description herein, that the disclosure can be practiced without one or more of the specific features or advantages of a particular embodiment. In other instances, additional features and advantages may be recognized in certain embodiments that may not be present in all embodiments of the present disclosure.

Reference throughout this specification to "one embodiment", "an embodiment", or similar language means that a particular feature, structure, or characteristic described in connection with the indicated embodiment is included in at least one embodiment of the present disclosure. Thus, the phrases "in one embodiment", "in an embodiment", and similar language throughout this specification may, but do not necessarily, all refer to the same embodiment.

Reference throughout this specification to the term "distal" refers to a system, device, component, end, portion, or segment that is disposed closer to a patient and/or further from a console during an ophthalmic procedure; and the term "proximal" refers to the system, device, component, end, portion, or segment that is disposed further from the patient and/or closer to the console during the ophthalmic procedure.

FIG. 1 illustrates a cross-sectional view of an exemplary eye 100 of a patient to facilitate understanding of the present disclosure. In FIG. 1, the eye 100 includes a retina 102, a lens 104, a cornea 106, and an iris 110. A lens capsule or capsular bag 112, located behind the iris 110 of the eye 100, contains the lens 104, which is seated between an anterior capsule segment or anterior capsule 114 and a posterior capsular segment or posterior capsule 116. The anterior capsule 114 and the posterior capsule 116 meet at an equatorial region 118 of the lens capsule 112. The lens capsule 112 is attached to a ciliary body 124 via zonule fibers 126, which hold the lens capsule 112 in place. The eye 100 also includes an anterior chamber 120 located in front of the iris 110 and a posterior chamber 122 located between the iris 110 and the lens capsule 112.

Behind the lens capsule 112 is an intraocular space 130 containing vitreous humor, which is surrounded by a hyaloid membrane that is disposed on the retina 102, the ciliary body 124, and the posterior capsular 116. The retina 102 is disposed against a choroid 132, which is disposed against a sclera 134. On inner walls of the choroid 132 is a pars plana 140. The pars plana 140 is a region forming a transition between the ciliary body 124 and the retina 102. The pars plana 140 may be a circumferential band around an inner circumference of the eye 100. As an example, a diameter of the pars plana 140 may be 3 millimeters (mm) to 5 mm.

A globe 138 of the eye 100, or eyeball, is defined by an outer surface of the eye 100 apart from any appendages, such that the globe 138 has a substantially spherical, yet slightly elongated, shape. That is, the globe 138 may be described as a prolate spheroid because the globe 138 is slightly flattened along its posterior-anterior axis. Individual variations in the globe 138 may exist that affect the overall shape and curvature of the eye 100. For example, individuals with an astigmatism may have a deviation in curvature (e.g., more or less curvature) of the globe 138 as compared to individuals without astigmatism.

The eye 100 is disposed within an orbit 136 (also referred to as an "orbital cavity" or "eye socket"), which is a bony cavity that surrounds and mechanically protects the eye 100. In certain embodiments, the orbit 136 is formed by several bones of the skull such as, for example, a frontal bone, a maxilla, a zygomatic bone, a lacrimal bone, an ethmoid bone, a sphenoid bone, and a palatine bone. The orbit 136 has a roughly conical shape with a posterior apex and an anterior base, such that a posterior portion of the orbit 136 has more separation from the eye 100 than an anterior portion of the orbit 136. Additionally, the orbit 136 surrounds extraocular muscles 144, which are connected at a posterior surface of the sclera 134 and are configured to control movement of the eye 100, and fat pads 146, which provide cushioning for the eye 100 in the orbit 136. The orbit 136 also houses blood vessels, nerves, connective tissues, layers of soft tissue (e.g., periosteum, orbital fat, and orbital septum), which help protect and support the eye 100.

Referring back now to the interior of the eye 100, the retina 102 is disposed along a posterior region of the intraocular space 130. The retina 102 is responsible for capturing light that enters the eye 100 for translation into images seen by the patient. The retina 102 generally includes a plurality of layers, an innermost layer being an inner limiting membrane (ILM), and an outermost layer being the choroid 132. Between the ILM and the choroid 132 are a retinal nerve fiber layer (NFL), a ganglion cell layer (GCL) comprising ganglionic cells, an inner plexiform layer or inner synaptic layer (IPL) and an inner nuclear layer (INL) comprising amacrine, bipolar, and horizontal cells, an outer plexiform layer or outer synaptic layer (OPL), an outer nuclear layer (ONL), an external limiting membrane (ELM), photoreceptor outer and inner segments (IS/OS) with photoreceptors (e.g., rods and cones), a retinal pigment epithelium (RPE) layer, and Bruch's membrane (BM). Generally, a full-thickness of the retina 102 may refer to all retinal layers from the ILM to the RPE, BM, and/or the choroid 132.

A peripheral area 142 of the retina 102 (referred to herein as "peripheral retina 142") encompasses a portion of the retina 102 that extends beyond a macula 148 and an optic nerve 150, i.e., the portions of the retina 102 involved in central vision. The peripheral retina 142 is located towards the outer edges of the retina 102 and extends towards the ciliary body 124 before merging with the choroid 132. Although the peripheral retina 142 contains fewer cones and more rods than a central portion of the retina 102, the peripheral retina 142 plays an important role in overall vision by contributing to motion perception, detection of periphery objects, and creating a wider field of view. Thus, the peripheral retina 142 helps provide contextual information about the patient's visual environment.

The peripheral retina 142 may be subject to various retinal conditions and abnormalities. For example, retinal tears, retinal detachments, peripheral retinal degenerations, lattice degeneration, peripheral retinal holes, and other peripheral retinal abnormalities frequently affect the peripheral retina 142. As such, applying pressure to the peripheral retina 142 is critical to detecting such retinal conditions and abnormalities. Inwards movement of the peripheral retina 142 may also be useful for performing procedures (e.g., peripheral vitrectomy procedures, such as shaving as listed in the examples) thereon or near the peripheral retina 142. However, assessing the peripheral retina 142 may be particularly challenging due to its location and limited accessibility. To examine the peripheral retina 142, surgeons and/or skilled assistants may employ scleral depression techniques.

Scleral depression is a technique commonly used in ophthalmology to examine the peripheral retina 142 and the intraocular space 130. In certain cases, scleral depression involves applying pressure to the sclera 134 using a scleral depressor or indentation tool. As an example, the scleral depressor or indentation tool may be used to apply pressure directly to the sclera 134, or to the extraocular muscles 144 and/or the fat pads 146, which compress against the sclera 134. Applying pressure to the sclera 134 allows a surgeon or skilled assistant to examine the peripheral retina 142 more clearly by moving the retina 102 and/or the periphery of the eye 100 into view of the surgeon (e.g., via inward tissue displacement), and to determine whether there may be any retinal conditions and/or abnormalities. However, current scleral depression techniques present a variety of limitations.

During certain ophthalmic surgical procedures, such as bimanual vitreoretinal surgical procedures, a skilled assistant may be needed to perform scleral depression while the surgeon performs other operations of the procedure with both hands. For example, in one common approach to vitreous shaving, a skilled assistant indents the sclera with a scleral depressor while a surgeon shaves the vitreous base with a vitrector in one hand and a light pipe in the other hand (e.g., a bimanual surgery technique). Although this bimanual surgery technique enables relatively effective vitreous shaving and safe eye control, it relies on the skill and presence of the assistant.

Further, although the surgeon can use a chandelier-based lighting port and perform scleral depression with one hand while using a vitrector in the other hand, such a setup may provide inefficient lighting in intraocular spaces and increase the risk of tortional rotation. For example, chandelier lighting may not efficiently illuminate 360° around an intraocular space and posterior-to-anterior pathology, as compared to a light pipe. Moreover, the use of a single intraocular instrument, i.e., a vitrector, increases the risk of unintentional tortional rotation of the patient's eye.

In certain examples, a surgeon may use a lighted depressor to perform scleral depression with one hand, while performing vitreous shaving with a vitrector in the other hand. However, the amount of light reaching the retina from scleral transillumination may be significantly limited, leading to suboptimal shaving, particularly in patients with more pigmented fundi. Furthermore, utilization of the vitrector still presents an elevated risk of tortional rotation of the eye due to use of one instrument intraocularly.

Accordingly, the devices described herein overcome many of the limitations associated with current techniques for scleral depression.

Certain embodiments described herein provide improved scleral depression devices for use during performance of ophthalmic procedures, including peripheral vitrectomies and other vitreoretinal surgical procedures. More particularly, certain embodiments provide hands-free scleral depression devices that facilitate the indentation of a patient's sclera without necessitating the presence of an assistant to perform the indentation, and which eliminate the visual and/or instrumental impedances caused by conventional scleral depression techniques.

Certain embodiments of the present disclosure are directed to a scleral depression device. In some embodiments, the scleral depression device includes a ring defining an opening with a diameter that is at least 6 to 8 mm long, where the ring includes a handle for rotating the scleral depression device about a vertical axis through an eye, and one or more arms protruding from the ring, where the one or more arms are configured to be disposed over a globe of the eye for controllable depression of a sclera of the eye. In certain embodiments, the one or more arms comprise a depression feature at a distal end of each of the one or more arms. As described herein, the depression feature may be a spherical knob, a semispherical knob, an arched bar, or other similar feature. In certain examples, the depression features may each laterally extend up to about three or four clock hours around the globe, or a circumference, of the eye. For example, each depression feature may extend between about one clock hour and about three clock hours around the globe, or a circumference, of the eye.

By using a scleral depression device including a ring and one or more arms configured to be disposed over a globe of an eye for controllable depression of a sclera of the eye, the scleral depression device may allow for 360° rotation and posterior-to-anterior sliding capabilities. Additionally, the scleral depression device may be easily applied and removed without the need for a skilled assistant. During scleral depression, the scleral depression device may not impede on other surgical instruments or microscopic movement, nor impede on a surgeon's intraoperative visualization. Thus, the surgeon may be capable of performing bimanual surgery while operating without the use of a fourth chandelier lighting port.

Figure 2A:
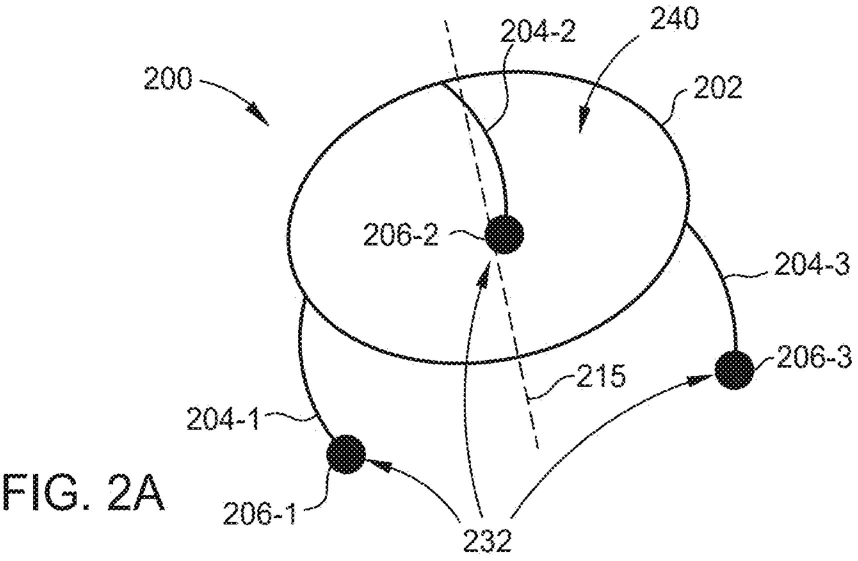
FIG. 2A is a top side isometric view illustrating an example scleral depression device having three arms, according to certain embodiments.
Figure 2B:
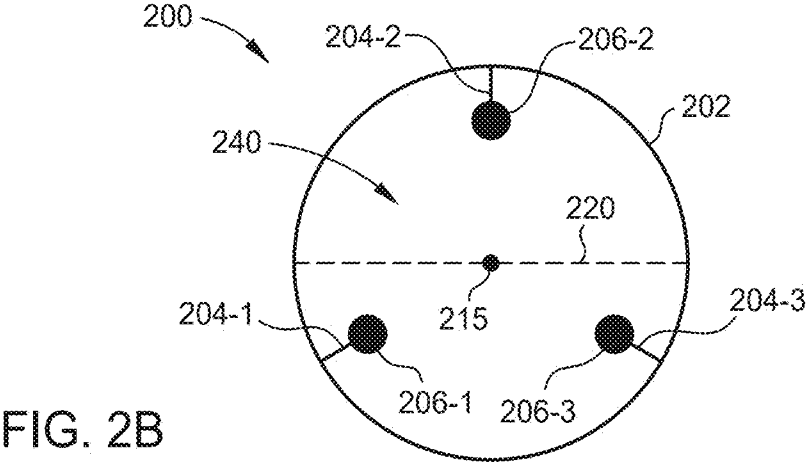
FIG. 2B is a bottom up perspective view illustrating the scleral depression device of FIG. 2A, according to some embodiments.
Figure 2C:
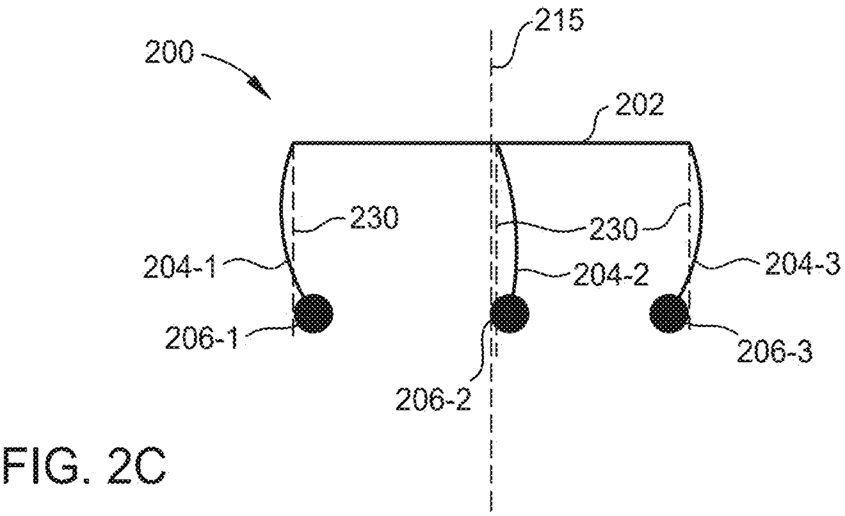
FIG. 2C is a side perspective view illustrating the scleral depression device of FIG. 2A, according to some embodiments.

FIGS. 2A-2C illustrate various views of an example scleral depression device 200 comprising a ring and three arms, according to certain embodiments.

Turning to FIG. 2A, a top side isometric view of scleral depression device 200 is shown. The scleral depression device 200 comprises a ring 202 coupled to three arms 204: a first arm 204-1, a second arm 204-2, and a third arm 204-3. Each arm 204 is coupled to a depression feature 206: first arm 204-1 is coupled to a first depression feature 206-1, second arm 204-2 is coupled to a second depression feature 206-2, and third arm 204-3 is coupled to a third depression feature 206-3. In certain embodiments, the depression features 206 are knobs, beads, or bars. Additionally, although the scleral depression device 200 is shown as including three arms 204-1, 204-2, and 204-3, the scleral depression device 200 may also include more than three arms (e.g., as shown in FIG. 3E) or less than three arms (e.g., as shown in FIG. 3F). In other words, the scleral depression device 200 may include one or more arms 204.

In certain embodiments, the ring 202 has a circular or annular shape, as shown in FIG. 2A. In some embodiments, the ring 202 may be ovate, triangular, rectangular, or have any other suitable shape. The ring 202 generally defines an opening 240 configured to provide visual or instrumental access when disposed over the eye 100, and facilitates a base or attachment point for the arms 204. For example, the surgeon or skilled assistant may examine and/or operate on the eye 100 through the opening 240. Accordingly, a diameter or dimension of the opening 240 may be larger than, or at least 3 mm larger than, an outer diameter of the pars plana 140 of the eye 100 (as seen in FIG. 2B), such that an inner circumference of the ring 202 is disposed radially outward of an outer circumference of the pars plana 140. As described above, the diameter of the pars plana 140 in an average eye may be 3 millimeters (mm) to 5 mm. Therefore, as an example, the diameter of the opening 240 is at least 6 mm to 8 mm long (e.g., 6.2 mm, 6.8 mm, 7.2 mm, 7.8 mm, etc.), but can be longer than 8 mm (e.g., 8.2 mm, 8.8 mm, 9 mm, 9.2 mm, 9.8 mm, etc.). In some embodiments, the ring 202 is comprised of a metallic material, such as titanium, nitinol, cobalt-chromium-aluminum-silicon (CCAS), stainless steel, and other alloys. In some embodiments, the ring 202 is comprised of a thermoplastic polymeric material, such as polycarbonate, polypropylene, polyethylene, and other thermoplastics. Generally, the ring 202 may be rigid or have some elasticity.

The arms 204 are generally configured to be slipped and disposed over the globe 138 of the eye 100 for controllable depression of the sclera 134. To facilitate the placement of the arms 204 over the globe 138, the arms 204 may each be comprised of an elastic material to facilitate their outward expansion and inward contraction as the arms 204 are slipped over the globe 138 during use. For example, each of the arms 204 may be formed of an elastic metallic or thermoplastic polymer material, or other suitable material enabling a slight pliability of the arms 204. Examples of suitable materials for the arms 204 include titanium, nitinol, cobalt-chromium-aluminum-silicon (CCAS), stainless steel, metallic alloys, polycarbonate, polypropylene, polyethylene, and other thermoplastics. In certain embodiments, one or more of the arms 204 are formed of the same material as the ring 202. In certain embodiments, one or more of the arms 204 are formed of a material different from that of the ring 202.

In certain embodiments, the arms 204 may each extend or protrude from the ring 202 in a first, distal direction, e.g., in the same direction. In such embodiments, the first direction is parallel to a vertical axis 215 passing through the center of the opening 240 of the scleral depression device 200. In certain other embodiments, the arms 204 may each extend from the ring 202 at an angle relative to the vertical axis 215.

In certain embodiments, each of the arms 204 comprises a curvature for conforming to the globe 138 of the eye 100. The curvature of each of the arms 204 can be adjustable in certain embodiments. For example, in certain embodiments, the arms 204 are malleable and can be adjusted manually by a user to achieve more or less depression of the sclera 134. In some embodiments, the curvature of each of the arms 204 causes a distal end 232 of the arms 204 to protrude inwards towards a center point of the ring 202 (as seen in FIG. 2B). The curvature of the arms 204 may be preset during manufacturing, and/or adjusted and set by a user prior to, or during use of the scleral depression device 200. By allowing the curvature of the arms 204 to be adjusted, the scleral depression device 200 can be altered to better fit certain eye shapes and/or surgical conditions. In some embodiments, the curvature of each of the arms 204 may be the same or different from one or more other arms 204, such that each arm may have its own curvature. Independent curvatures of each arm 204 may be particularly useful for improving comfort of the patient when the scleral depression device 200 is applied to an eye with an astigmatism.

In certain embodiments, the arms 204 are equidistantly positioned around a circumference of the ring 202. Equidistantly positioning the arms 204 around the ring enables uniform depression of the sclera 134 when the scleral depression device 200 is applied to the eye 100. The arms 204 may also be positioned at different circumferential distances from each other. For example, the first arm 204-1 and the second arm 204-2 may be equally distant from the third arm 204-3, but not from each other.

The depression features 206 are configured to apply pressure against the sclera 134 of the eye 100 to induce depression of the sclera 134. In some embodiments, the depression features 206 include beads positioned at a distal end of each of the arms 204. For example, the depression features 206-1, 206-2, and 206-3 are positioned at an end of the arms 204-1, 204-2, and 204-3, respectively, that is furthest from the ring 202.

In certain embodiments, the depression features 206 each have a rounded or spherical shape. In such embodiments, the rounded edges of the depression features 206 may improve comfort for the patient when the scleral depression device 200 is applied to the eye 100, and may further reduce trauma, such as scraping, to the sclera 134 when being positioned along the eye 100. In certain examples, each depression feature 206 may laterally extend up to about three or four clock hours around the globe, or a circumference, of the eye 100.

In some embodiments, there may be multiple depression features 206 disposed along a length of one or more of the arms 204-1, 204-2, and/or 204-3. For example, there may be one or more depression features 206 positioned along the length of an arm 204 between the ring 202 and the distal end of the arm 204. Additionally, although the depression features 206 are shown as spherical beads, one or more of the depression features 206 may also be ellipsoid, cylindrical, ring-like, or have some other prismatic shape. Other embodiments of depression features 206 are described with reference to FIG. 3A.

Further, in certain embodiments, one or more of the arms 204 and/or one or more of the depression features 206 may comprise an illumination device configured to illuminate the intraocular space 130 through the sclera 134. Examples of the illumination devices may include, but are not limited to, light-emitting diodes (LEDs), fiber optics (e.g., illumination fibers), and/or chemoluminescence materials. Light emitted by the illumination device may be directed inward towards a center point of the scleral depression device 200, e.g., toward a point along vertical axis 215. An example of the illumination device is described in further detail with reference to FIG. 5.

FIG. 2B is a bottom up perspective view illustrating the scleral depression device 200 seen in FIG. 2A along vertical axis 215. As shown in FIG. 2B, the opening 240 has a diameter 220, and the distal ends 232 of the arms 204 protrude inwards towards a center point of the ring 202. The diameter 220 may be at least larger than the pars plana 140 of the eye 100. Although the depression features 206 and the distal ends 232 are shown as converging to points inside an inner circumference of the ring 202 when viewed along the vertical axis 215, the depression features 206 may also be disposed outside an outer circumference of the ring 202 in certain embodiments.

FIG. 2C is a side perspective view illustrating the scleral depression device 200 seen in FIG. 2A. As shown in FIG. 2C, each of the arms 204-1, 204-2, and 204-3 have a length 230. The length 230 of the arms 204 may be defined as a distance between the distal end of the arms 204 and a point at which the arms 204 connect to the ring 202. The length 230 may extend beyond an outer perimeter of the pars plana 140 of the eye 100 when the scleral depression device 200 is placed over the eye 100. Although the arms 204-1, 204-2, and 204-3 are shown as having a same length, one or more of the arms 204 may also have different lengths from one or more other arms 204.

Although the scleral depression device 200 is described with various dimensions, the scleral depression device 200 can be manufactured to fit various orbit and fornix sizes. Additionally, the scleral depression device 200 may be configured to be sterilized for re-use, or configured to be disposed after use in ophthalmic procedures.

FIGS. 3A-3F illustrate alternative examples of scleral depression devices, according to certain embodiments.

Figure 3A:
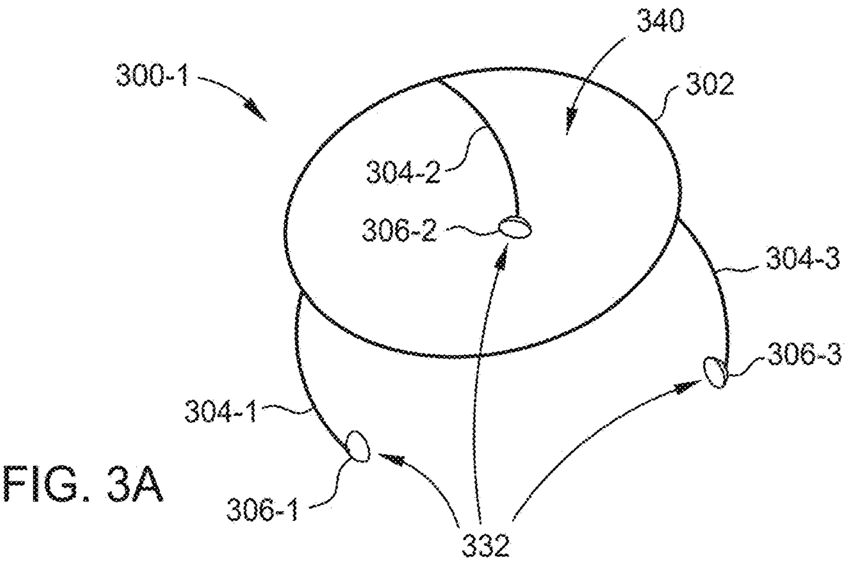
FIG. 3A is a top side isometric view illustrating another example scleral depression device having three arms, according to certain embodiments.

Turning to FIG. 3A, a top side isometric view of an example scleral depression 300-1 is shown. The scleral depression device 300-1 is an alternative to the scleral depression device 200 shown in FIGS. 2A-2C. Similar to scleral depression device 200, the scleral depression device 300-1 comprises a ring 302 with an opening 340, arms 304, and depression features 306.

However, as opposed to the scleral depression device 200 of FIGS. 2A-2C, the three depression features 306 shown in FIG. 3A are semispherical knobs. In other words, the depression features 306 may be a semi-circular, bowl-like, or other curved three-dimensional shape that conforms to the globe 138 of the eye 100. In some embodiments, there may be multiple depression features along a length of one or more of the arms 304-1, 304-2, and/or 304-3. In certain examples, each depression feature 306 may laterally extend up to about three or four clock hours around the globe, or a circumference, of the eye 100.

Figure 3B:
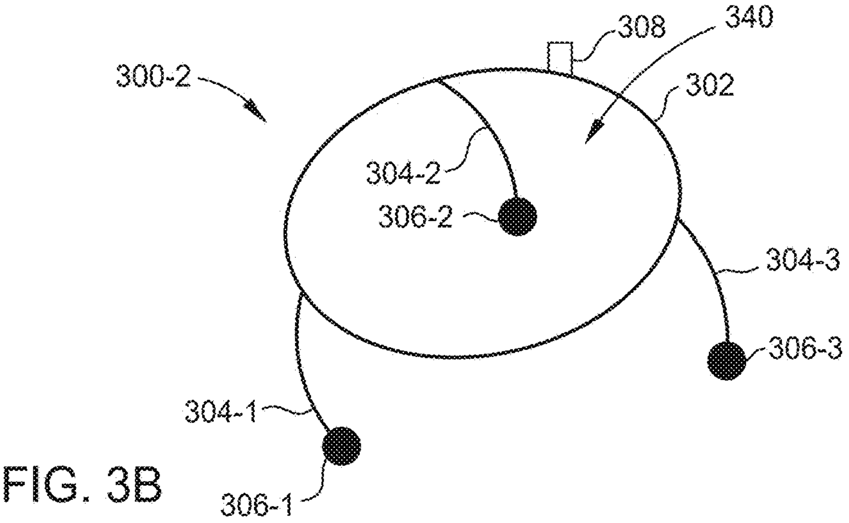
FIG. 3B is a top side isometric view illustrating an example scleral depression device having three arms and a handle, according to certain embodiments.

FIG. 3B is a top side isometric view illustrating another example scleral depression device 300-2. Similar to scleral depression device 300-1, the scleral depression device 300-2 is an alternative embodiment of the scleral depression device 200 shown in FIGS. 2A-2C, and comprises a ring 302 with an opening 340, arms 304, and depression features 306, as also described with reference to FIGS. 2A-2C.

However, as opposed to the scleral depression device 200 of FIGS. 2A-2C, the scleral depression device 300-2 shown in FIG. 3B further comprises a handle 308. In certain embodiments, the handle 308 protrudes from the ring 302 in a second direction away from the arms 304. For example, the handle 308 may protrude from the ring 302 at an angle of at least 90° (e.g., 90°-180°, 100°-170°, 110°-160°, or) 120°-150° relative to the arms 304. The handle 308 may protrude from the ring 302 at any point along a circumference of the ring 302. Although a single handle 308 is shown in FIG. 3B, the scleral depression device 300-2 may include more than one handle at any point(s) along the circumference of the ring 302.

In certain embodiments, the handle 308 may be configured to provide an ergonomic holding point for a surgeon or skilled assistant when positioning and orienting the scleral depression device 300-2 during application to the eye 100. As an example, the handle 308 may be used to rotate the scleral depression device 300-2 at least up to 130° in a clockwise direction or a counter counterclockwise direction about a vertical axis of the eye 100 after the scleral depression device is slid over/around the eye 100 to move the ring 302, the arms 304, and the depression features 306 to a desired position. As another example, the handle 308 may be held by the surgeon or skilled assistant to facilitate sliding of the scleral depression device 300-2 over the eye 100. Accordingly, the handle 308 may be a rectangular shape, a cylindrical shape, a ring-like shape, or any other suitable shape, and may include knurling, ribbing, tapers, and/or other features to facilitate improved gripping thereof by the surgeon or assistance.

Figure 3C:
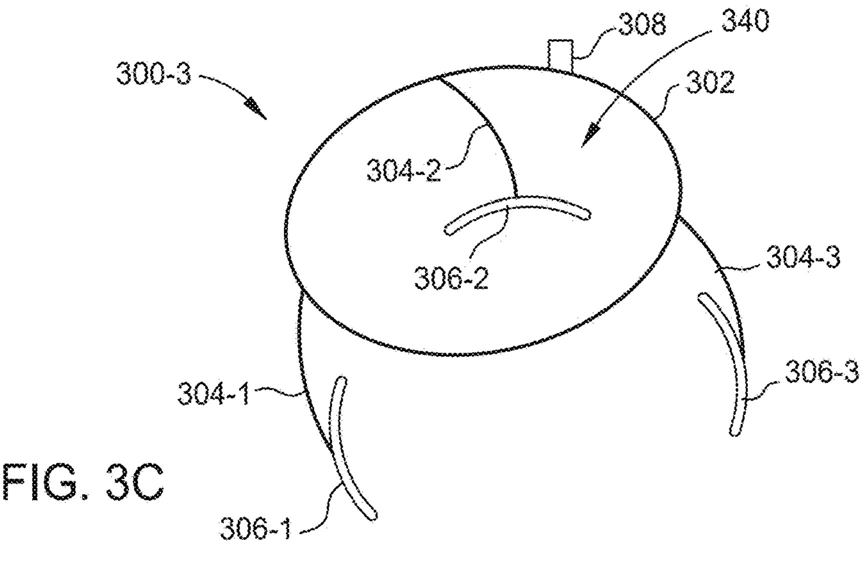
FIG. 3C is a top side isometric view illustrating another example scleral depression device having three arms and a handle, according to certain embodiments.

FIG. 3C is a top side isometric view illustrating another example scleral depression device 300-3. The scleral depression device 300-3 is an alternative embodiment of the scleral depression device 300-2 shown in FIG. 3B, and comprises a ring 302 with an opening 340, arms 304, depression features 306, and a handle 308, as described with reference to FIG. 3B.

However, as opposed to the scleral depression device 300-2 of FIG. 3B, the depression features 306 shown in FIG. 3C are arched bars. Generally, the arched bars may resemble curved cylinders having curvatures that conform to the globe 138 of the eye 100. In certain examples, the arched bars may each laterally extend up to about three or four clock hours around the globe, or a circumference, of the eye.

Figure 3D:
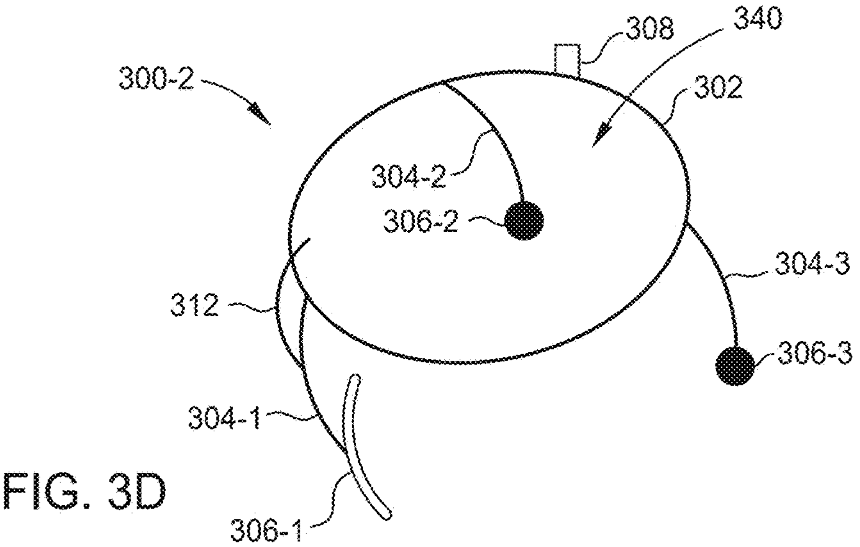
FIG. 3D is a top side isometric view illustrating an example scleral depression device having three arms and a combination of depression features, according to certain embodiments.
Figure 3E:
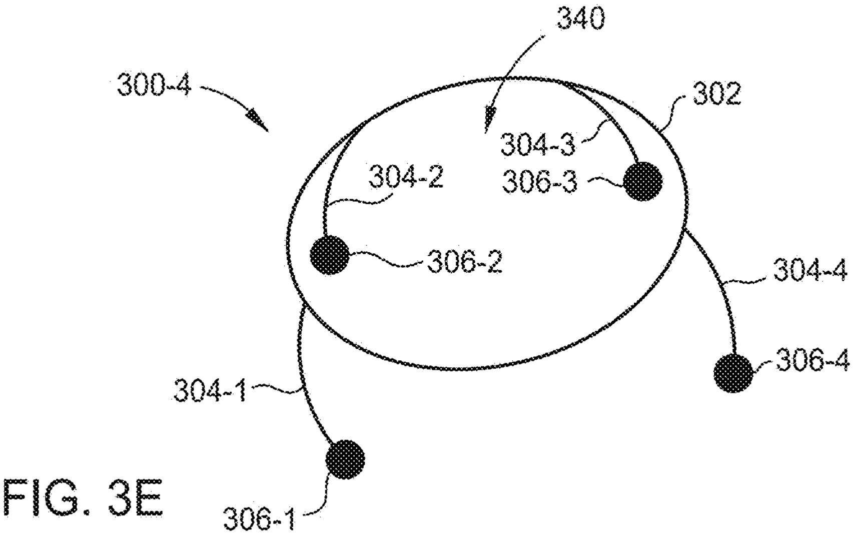
FIG. 3E is a top side isometric view illustrating an example scleral depression device having four arms, according to certain embodiments.
Figure 3F:
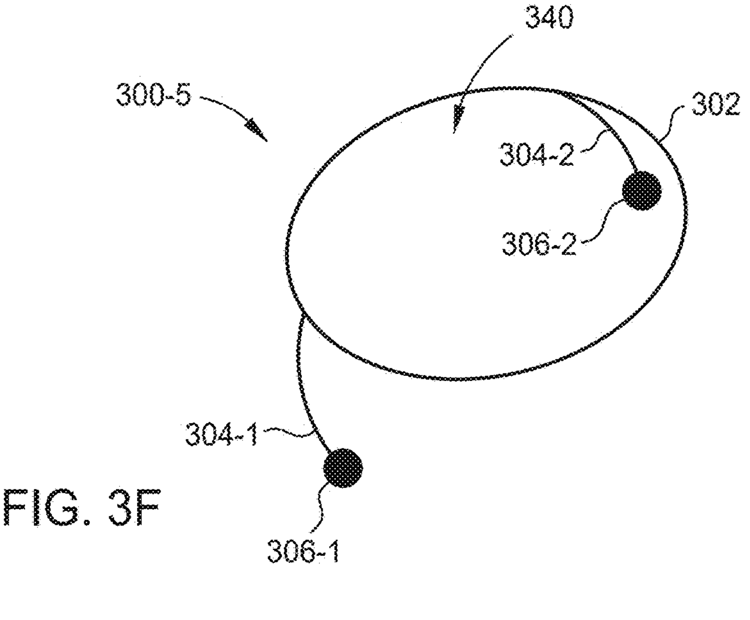
FIG. 3F is a top side isometric view illustrating an example scleral depression device having two arms, according to certain embodiments.

FIG. 3D is a top side isometric view illustrating another example scleral depression device 300-4. The scleral depression device 300-4 is an alternative embodiment of the scleral depression device 300-1 shown in FIG. 3A, and comprises a ring 302 with an opening 340, and three arms 304-1, 304-2, and 304-3, as described with reference to FIG. 3A.

However, as opposed to the scleral depression device 300-1 of FIG. 3A, the scleral depression device 300-4 shown in FIG. 3D comprises a combination of different types of depression features 306-1, 306-2, and 306-3, similar to those described with reference to FIGS. 2A and 3C. In certain embodiments, a first depression feature 306-1 is an arched bar, and a second depression feature 306-2 and a third depression feature 306-3 include knobs. However, the depression features 306 may include any combination of different types depression features.

In certain embodiments, the first depression feature 306-1 is a primary depression feature used to depress the sclera 134, whereas the second depression feature 306-2 and the third depression feature 306-3 are secondary depression features used to stabilize or secure the scleral depression device 300-4 while positioned on the eye 100. In this instance, the primary depression feature is a unique or individual knob that may be larger and/or extend further about an outer circumference or globe 138 of the eye 100 as compared to the secondary depression features. Additionally, the scleral depression device 300-4 can have two or more primary depression features (e.g., with different depression features), less or more than two secondary depression features, and/or less or more than three arms 304.

Further, the scleral depression device 300-4 shown in FIG. 3D comprises a tab 312 extending outward and upward from the first arm 304-1. The tab 312 may extend from the first arm 304-1 past the ring 302 by a length of, for example, 3 mm to 15 mm (e.g., 4 mm to 14 mm, 5 mm to 13 mm, or 6 mm to 12 mm). A surgeon or other skilled assistant can use the tab 312 to manipulate or adjust the arm 304-1 and the first depression feature 306-1. For example, while the scleral depression device 300-4 is positioned on the eye (e.g., as seen in FIG. 4B), the surgeon can use the tab 312 to move the first arm 304-1 and the first depression feature 306-1 away from, towards, and/or around on the sclera of the eye. Adjustability and manipulation of the first arm 304-1 and the first depression feature 306-1 can improve the surgeon's visual and instrumental access to peripheral areas of the eye.

FIG. 3E is a top side isometric view illustrating another example scleral depression device 300-5. The scleral depression device 300-5 is an alternative embodiment of the scleral depression device 200 shown in FIGS. 2A-2C and comprises a ring 302 with an opening 340 as described with reference to FIGS. 2A-2C.

However, as opposed to the scleral depression device 200 of FIGS. 2A-2C, the scleral depression device 300-5 shown in FIG. 3E comprises four arms 304 (a first arm 304-1, a second arm 304-2, a third arm 304-3, and a fourth arm 304-4) and four depression features 306 (a first depression feature 306-1, a second depression feature 306-2, a third depression feature 306-3, and a fourth depression feature 306-4). In certain embodiments, the four arms 304-1, 304-2, 304-3, and 304-4 are equidistantly positioned around the ring 302. The depression features 306 in FIG. 3E may also be semispherical knobs or arched bars, as described with reference to FIGS. 3A and 3D, respectively.

FIG. 3F is a top side isometric view illustrating another example scleral depression device 300-6. Similar to scleral depression device 300-5, the scleral depression device 300-6 is an alternative embodiment of the scleral depression device 200 shown in FIGS. 2A-2C and comprises a ring 302 with an opening 340 as described with reference to FIGS. 2A-2C.

However, as opposed to the scleral depression device 200 of FIGS. 2A-2C, the scleral depression device 300-6 shown in FIG. 3F comprises two arms 304 (a first arm 304-1 and a second arm 304-2) and two depression features 306 (a first depression feature 306-1 and a second depression feature 306-2). In certain embodiments, the two arms 304-1 are 304-2 in FIG. 3F are equidistantly positioned around the ring 302. For example, the first arm 304-1 and the second arm 304-2 may be positioned at opposing points of the ring 302 (e.g., 180° from each other along the ring 302). In certain other embodiments, the two arms 304-1 and 304-2 in FIG. 3F are positioned less than/more than 180° from each other along the ring 302.

Examples of operations for applying and positioning the present scleral depression devices onto an eye are described in further detail below with reference to FIGS. 4A-4E.

Figure 4A:
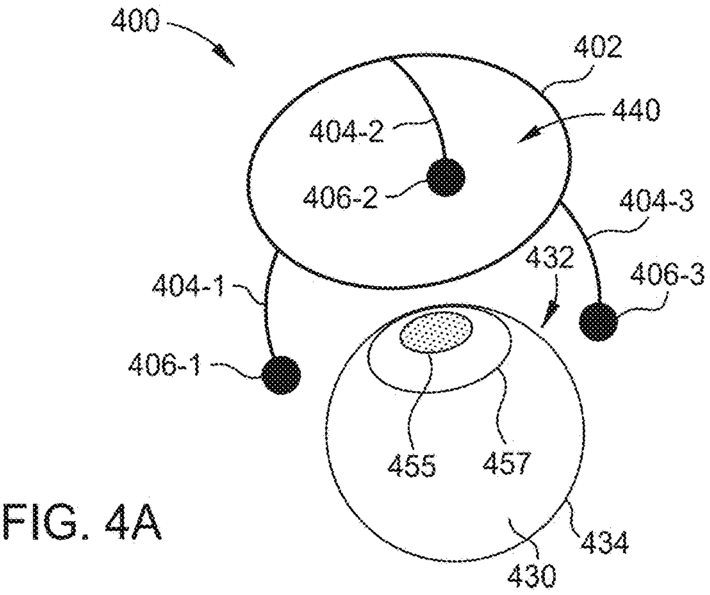
FIGS. 4A-4C illustrate operations for applying a scleral depression device to an eye, according to some embodiments herein.
Figure 4B:
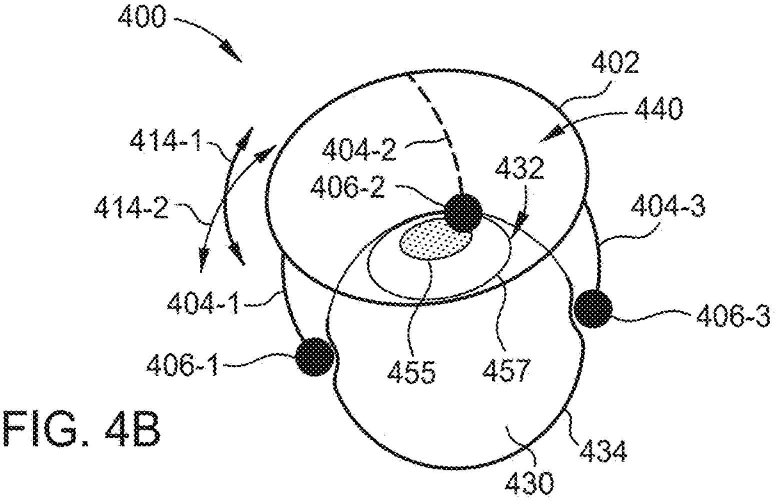

FIG. 4A illustrates a first operation for applying a scleral depression device 400 to an eye 430. The eye 430 may be as described with reference to the eye 100 shown in FIG. 1. That is, the eye 430 includes a globe 432 and a sclera 434 and is positioned within an orbit 436. The scleral depression device 400 is similar to scleral depression device 200 shown in FIGS. 2A-2C. That is, the scleral depression device 400 includes a ring 402 with an opening 440, and three arms 404 (404-1, 404-2, and 404-3 are shown), each including depression features 406 (406-1, 406-2, and 406-3, respectively). Although the scleral depression device 400 represents an embodiment of the scleral depression device 200 shown in FIGS. 2A-2C, the scleral depression device 400 may also be any one of scleral depression devices 300-1, 300-2, 300-3, 300-5, or 300-6 shown in FIGS. 3A-3F.

In FIG. 4A, the scleral depression device 400 is first positioned adjacent to an anterior portion of the eye 430 and optionally rotationally oriented such that one or more depression features 406 are rotationally aligned with a position on the sclera 434 to be depressed. In some embodiments, the scleral depression device 400 is centered over the eye 430 as it is introduced, such that a center point of the ring 402 aligns with a center point of the eye 430, e.g., center of pupil 455 and iris 457. As such, the arms 404 may be positioned circumferentially around the eye 430, and the depression features 406 may laterally align with a space between the eye 430 and the orbit 436. In some embodiments, a surgeon or a skilled assistant may introduce the scleral depression device 400 to the eye 430.

In some embodiments, a lubricant may be applied to the scleral depression device 400 and/or the eye 430 before the scleral depression device 400 is applied to the eye 430. The lubricant(s) may help facilitate application of the scleral depression device 400 onto the eye 430 and improve comfort during application.

FIG. 4B illustrates a second operation for applying the scleral depression device 400 to the eye 430. In FIG. 4B, the scleral depression device 400 has carefully advanced (e.g., slid, pressed, pushed, etc.) onto and over the globe 432 of the eye 430 so as to avoid trauma to surrounding tissues. When the scleral depression device 400 is advanced onto the eye 430, the arms 404 and the depression features 406 may be evenly distributed around the globe 432 of the eye 430. As such, the depression features 406 may begin to depress the sclera 434 of the eye 430 as the scleral depression device 400 is advanced.

The position of the scleral depression device 400 as shown in FIG. 4B may be a final desired position where the scleral depression device 400 may be left while the surgeon performs an ophthalmic procedure. As such, the scleral depression device 400 may serve as a hands-free device. At this final position, one or more of the depression features 406 engage the sclera 434 of the eye 430 at desired position(s) along the globe 432 and depress the sclera 434 inwards, thereby bringing, e.g., the peripheral retina and/or other tissues of the peripheral fundus into view of the surgeon to facilitate performing the ophthalmic procedure.

In certain embodiments, while or after the scleral depression device 400 is advanced over the eye 430, the scleral depression device 400 may be rotated, e.g., via one or more handles, until the depression features 406 are in desired positions to indent the sclera 434. That is, the scleral depression device 400 may be rotated in a first direction 414-1 and/or in a second direction 414-2. The first direction 414-1 illustrates a clockwise or counter clockwise motion, and the second direction 414-2 illustrates a left/right motion over the top of the eye 430. This rotation of the scleral depression device 400 may be performed as needed before and in-between ophthalmic procedures to facilitate visualization of the peripheral fundus for the surgeon during such procedures.

Figure 4C:
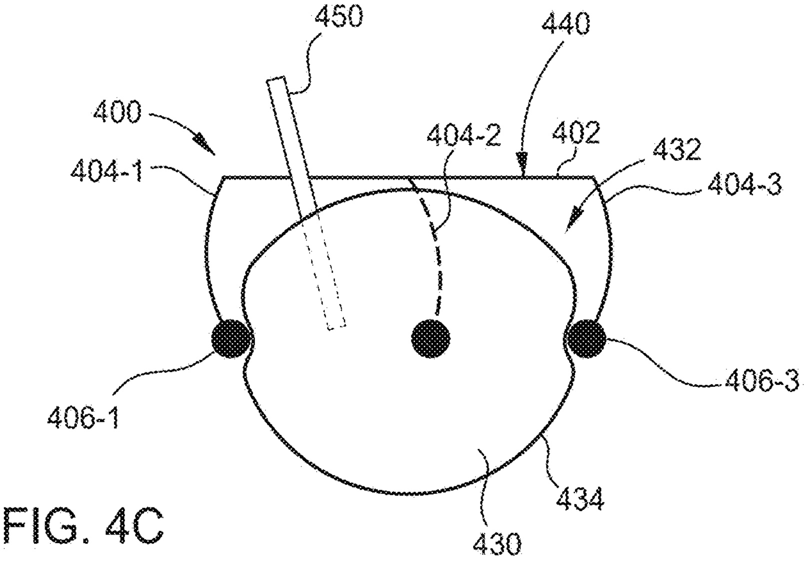

FIG. 4C illustrates a cross-sectional side perspective view of the scleral depression device 400 on the eye 430 at the final position described with reference to FIG. 4C. As shown in FIG. 4C, when the scleral depression device 400 is at the final position, the depression features 406 are positioned at a posterior portion of the eye 430 on the sclera 434.

At the final position, the ring 402 may provide ample space for the surgeon to insert a tool or instrument 450 into the eye 430 through the opening 440. For example, the surgeon may be able to access an interior portion of the eye 430 to perform ophthalmic procedures. The surgeon may also be able to access a proximal or distal exterior portion of the eye 430 by going through or around the opening 440.

After scleral depression has been performed on the eye 430, the scleral depression device 400 may be guided away from and removed from the eye 430. For example, the scleral depression device 400 may be removed from the eye 430 by sliding or pulling the scleral depression device 400 of the eye 430 without causing trauma to surrounding tissues.

Figure 5:
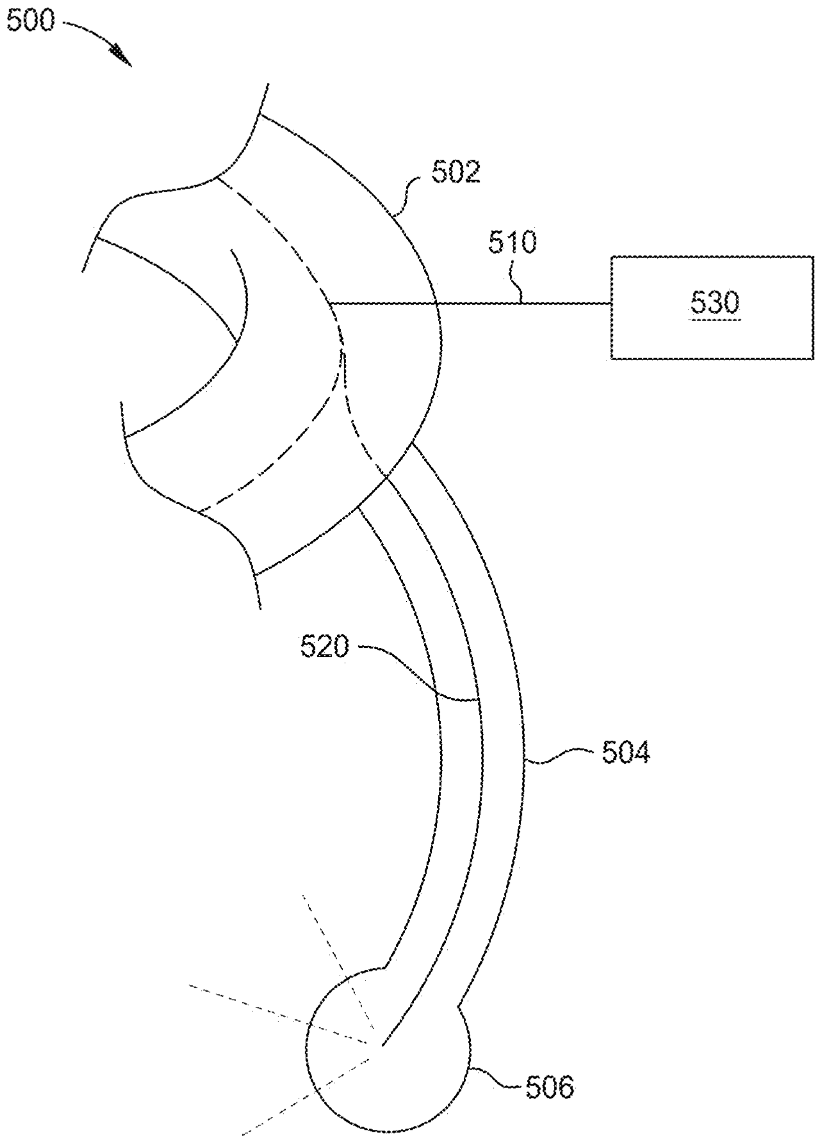
FIG. 5 is a cross-sectional side view illustrating an optical fiber within an arm of a scleral depression device, according to certain embodiments.

FIG. 5 is a cross-sectional side view illustrating an optical fiber 520 within an arm 504 of a scleral depression device 500, according to certain embodiments. As previously described, the scleral depression device 500 may comprise an illumination device such as, for example, an illumination optical fiber 520. In certain embodiments, as shown in FIG. 5, the optical fiber 520 may extend the entire length of the arm 504 from the ring 502 to the depression feature 506. In other words, the optical fiber 520 may be run through the arm 504 and the depression feature 506 of the scleral depression device 500. In certain embodiments, the optical fiber 520 may only extend along a partial length of the arm 504 and/or depression feature 506. The optical fiber 520 may also be disposed within the ring 502 of the scleral depression device 500 and/or other arms of the scleral depression device.

To provide sufficient illumination from within the arm 504 and the depression feature 506, at least a portion of the arm 504 and/or the depression feature 506 may be translucent, transparent, or at least semi-transparent. As such, at least a portion of the arm 504 and/or the depression feature 506 may be comprised of a polymeric material or other similar material that permits light to illuminate therethrough. In certain embodiments, an inner surface of the arm 504 and/or the depression feature 506 (e.g., facing the eye) is translucent, transparent, or at least semi-transparent, while an outer surface thereof is opaque.

In certain embodiments, the optical fiber 520 may be coupled to an illumination source 530 external to the scleral depression device 500. For example, the optical fiber 520 may be optically coupled to an illumination source 530 disposed within a surgical console. The optical fiber 520 may be optically coupled to the illumination source 530 via an optical fiber cable 510 extending from the illumination source 530 to the ring 502, or a via an optical fiber cable 510 extending from the illumination source 530 to a joint where the arm 504 connects to the ring 502 of the scleral depression device 500. In still other embodiments, scleral depression device 500 may comprise an LED light source disposed in a depression feature 506, an arm 504, or the ring 502.

The detailed description and the drawings are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims.

Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments may fall within the scope of the appended claims.

What is claimed is:

1. A device for scleral depression, the device comprising:

a ring defining an opening with a diameter of 6 to 8 millimeters (mm); and at least three arms protruding from the ring in a first direction, the at least three arms being equidistantly positioned around a circumference of the ring;

wherein each of the at least three arms have a curvature configured to conform to a globe of an eye and each of the at least three arms extends radially inward from the ring such that a distal end of each arm lies inside an inner circumference of the ring, and wherein the at least three arms are configured to be disposed over the globe of the eye for controllable depression of a sclera of the eye.

2. The device of claim 1, wherein the ring comprises a handle protruding in a second direction away from the at least three arms.

3. The device of claim 1, wherein the at least three arms are comprised of an elastic metallic material or a thermoplastic polymer material configured to conform to the globe of the eye.

4. The device of claim 1, wherein the at least three arms comprise an adjustable curvature for conforming to the globe of the eye.

5. The device of claim 1, wherein the at least three arms are equidistantly positioned around the ring to provide uniform depression of the sclera.

6. The device of claim 1, wherein the at least three arms are configured to extend beyond an outer perimeter of a pars plana of the eye.

7. The device of claim 1, wherein the at least three arms comprise:

four arms with a combination of different depression features at a distal end of each of the four arms.

8. The device of claim 1, wherein the at least three arms comprise:

a depression feature at a distal end of each of the at least three arms.

9. The device of claim 8, wherein the depression feature is a knob, a semispherical knob, or an arched bar.

10. The device of claim 8, wherein the depression feature of each of the at least three arms is configured to apply uniform pressure to the sclera.

11. The device of claim 8, wherein the depression feature of each of the at least three arms comprises an illumination source configured to illuminate the sclera.

12. The device of claim 8, wherein the depression features comprise chemiluminescent materials.

13. The device of claim 1, wherein the device is configured to rotate up to at least up to 150° in a clockwise direction or a counter counterclockwise direction about a vertical axis of the eye.

14. The device of claim 1, wherein the at least three arms are configured to be positioned between the globe and an orbit of the eye.

15. The device of claim 1, wherein the at least three arms have the same length.

16. The device of claim 1, wherein at least one of the at least three arms has a different length than at least one other arm of the at least three arms.

17. A device for scleral depression, the device comprising:

a ring defining an opening with a diameter that is about 6 to 8 millimeters (mm); and at least three arms protruding from the ring in a first direction, the at least three arms being equidistantly positioned around a circumference of the ring, wherein each of the at least three arms have a curvature configured to conform to a globe of an eye and each of the at least three arms extends radially inward from the ring such that a distal end of each arm lies inside an inner circumference of the ring, and wherein each of the at least three arms further comprise:

a depression feature at a distal end of each of the at least three arms, wherein the depression feature of each of the at least three arms are configured to apply pressure to a sclera of the eye to induce depression of the sclera, and wherein the at least three arms are configured to be disposed over the globe of the eye and to controllably induce the depression of the sclera for ophthalmic procedures.

18. The device of claim 17, wherein the at least three arms have the same length.

19. The device of claim 17, wherein at least one of the at least three arms has a different length than at least one other arm of the at least three arms.

20. A device for scleral depression, the device comprising:

a ring defining an opening with a diameter that is at least 6 to 8 millimeters (mm), wherein the ring comprises:

a handle for rotating the device about a vertical axis of an eye; and at least three arms protruding from the ring in a first direction, the at least three arms being equidistantly positioned around a circumference of the ring, wherein the at least three arms have a curvature configured to conform to a globe of an eye and each of the at least three arms extends radially inward from the ring such that a distal end of each arm lies inside an inner circumference of the ring, and wherein the at least three arms are configured to be disposed over the globe of the eye for controllable depression of a sclera of the eye.

* * * * *